United States Patent [19]
Clanton

[11] Patent Number: 4,979,616
[45] Date of Patent: Dec. 25, 1990

[54] SYRINGE DISPOSAL CONTAINER

[76] Inventor: Dennis L. Clanton, 1514 Centenary, Shreveport, La. 71104

[21] Appl. No.: 511,985

[22] Filed: Apr. 13, 1990

Related U.S. Application Data

[63] Continuation of Ser. No. 314,542, Feb. 23, 1989, abandoned.

[51] Int. Cl.$^5$ .............................................. B65D 81/02
[52] U.S. Cl. ..................................... 206/364; 206/523; 220/4 E
[58] Field of Search ....................... 206/364, 365, 523; 220/4 E

[56] References Cited

U.S. PATENT DOCUMENTS

| | | | |
|---|---|---|---|
| 620,434 | 2/1899 | Ermold | 206/365 X |
| 685,091 | 10/1901 | Becton | 206/365 |
| 3,181,693 | 5/1965 | Freistat | 206/523 |
| 3,491,914 | 1/1970 | Elzey | 206/365 X |
| 3,746,155 | 7/1973 | Seeley | 206/365 |
| 4,173,286 | 11/1979 | Stanko | 220/4 E |
| 4,219,693 | 8/1980 | French | 220/4 E |
| 4,512,474 | 4/1985 | Harding | 220/4 E |
| 4,524,868 | 6/1985 | Buckley et al. | 206/523 X |
| 4,664,259 | 5/1987 | Landis | 206/364 X |
| 4,671,408 | 6/1987 | Raines et al. | 206/45.23 X |

FOREIGN PATENT DOCUMENTS

| | | | |
|---|---|---|---|
| 1408369 | 7/1965 | France | 206/364 |
| 1529853 | 5/1968 | France | 220/4 E |
| 928857 | 6/1963 | United Kingdom | 220/4 E |
| 1158465 | 7/1969 | United Kingdom | 220/4 E |

Primary Examiner—William I. Price
Attorney, Agent, or Firm—Haynes and Boone

[57] ABSTRACT

A syringe disposal container which is characterized in a preferred embodiment by a bottom panel provided with upward-standing tabs along one side and on both ends and tab-receiving slots or seats spaced along the opposite side and also in the ends, with a syringe cradle formed therein to receive a syringe and needle. A top panel is also provided with downwardly-extending tabs along one side and on both ends thereof and is fitted with spaced tab slots or seats along the opposite side and in the ends and includes a receptacle which matches the cradle in the bottom panel, wherein the tabs in the bottom panel engage the seats in the top panel and the tabs in the top panel engage the seats in the bottom panel, to secure the top panel to the bottom panel and encapsulate the syringe inside the syringe cradle and the matching syringe receptacle.

29 Claims, 1 Drawing Sheet

U.S. Patent  Dec. 25, 1990  4,979,616
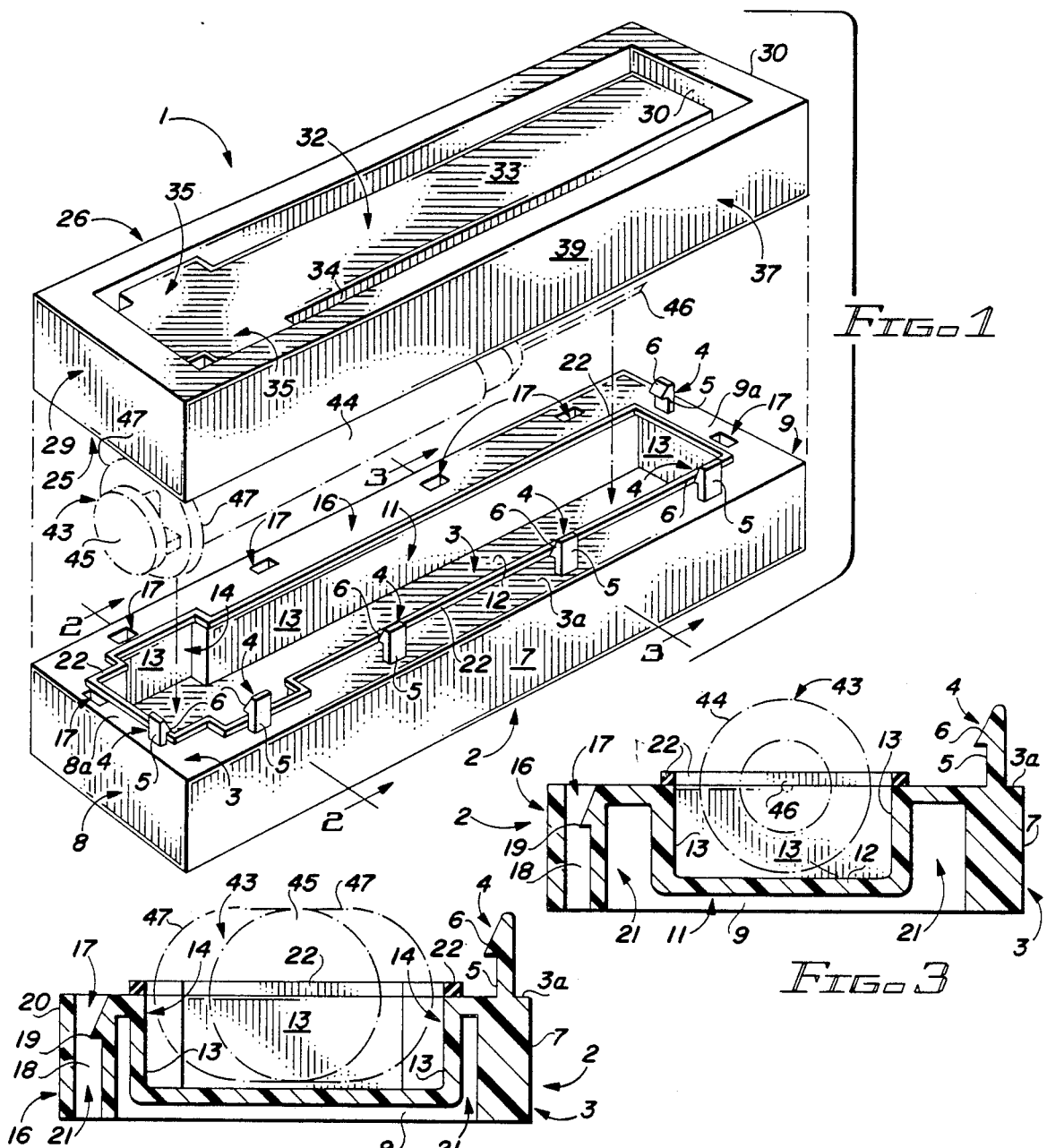
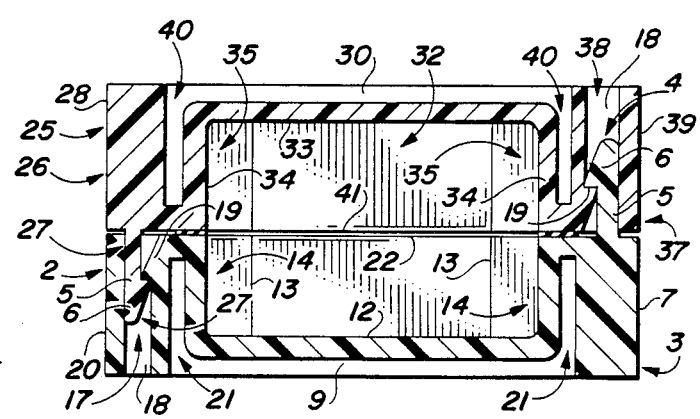

SYRINGE DISPOSAL CONTAINER

This is a continuation of Ser. No. 314,542, filed Feb. 23, 1989, now abandoned.

BACKGROUND OF THE INVENTION

FIELD OF THE INVENTION

This invention relates to the disposal of needle-carrying syringes and more particularly, to a syringe disposal container which is characterized in a preferred embodiment by matching top and bottom segments or panels, each provided with a cooperating depression, cavity or receptacle for receiving a needle-equipped syringe. The panels are also each fitted with extending tabs and corresponding tab seats for locking the top panel on the bottom panel and securing the syringe therebetween. In a most preferred embodiment of the invention the syringe disposal container is shaped of an injection-molded plastic material such as polyethylene or polypropylene. The top and bottom panel each include seals and upward-standing tabs spaced along one side and both ends, with tab seats located along the opposite side and both ends, respectively, such that closure of the top panel on the bottom panel in tab to tab seat-facing relationship engages the respective tabs with the oppositely-disposed tab seats and locks the top panel on the bottom panel to prevent leaking and re-opening. In another preferred embodiment of the invention a syringe cradle built into the bottom panel and a corresponding syringe receptacle located in the top panel are enlarged at one end of the syringe disposal container to receive the barrel flange of the syringe barrel.

One of the problems which has long been realized in the handling of syringes is the accidental pricking and sticking of fingers, arms and other parts of the body by contaminated needles after syringes are used to administer drugs or to draw blood from patients. This problem has become intensified in recent years with the spread of acquired immunity disease syndrome, or "AIDS", as well as periodic outbreaks of various strains of hepatitis. For example, Hepatitis "B" (previously called serum hepatitis) is a major and infectious occupational health hazard in the health-care industry and a model for the transmission of blood-borne pathogens. In 1985 the Centers for Disease Control (CDC) estimated that there were over 200,000 cases of Hepatitis "B" virus (HBV) infection in the United States each year, leading to 10,000 hospitalizations, 250 deaths due to fulminant hepatitis, 4000 deaths resulting from hepatitis-related cirrhosis and 800 deaths due to hepatitis-related liver cancer. The incidence of reported clinical Hepatitis "B" has been increasing in the United States and the hepatitis branch of the CDC has estimated that 500 to 600 health-care workers whose job entails exposure to blood are hospitalized annually, with over 200 deaths resulting from hepatitis, cirrhosis and liver cancer. Studies indicate that 10% to 40% of all health care or dental workers may show serologic evidence of past or present HBV infection. Health-care costs for Hepatitis "B" and Non-A, Non-B hepatitis in health-care workers were estimated to be 10 to 12 million dollars annually.

According to the most recent data available from the CDC, acquired immunodeficiency syndrome (AIDS) was the 13th leading cause of years of potential life lost in 1984, increasing to 11th place in 1985. As of Aug. 10, 1987, an accumulative total of 40,051 AIDS cases had been reported to the CDC, with 23,165 of those known to have died.

Since infection with HBV or human immunodeficiency virus (HIV) can lead to a number of life-threatening conditions, including cancer, researchers note that exposure to HBV and HIV should be reduced to the maximum extent feasible by engineering controls, work practices and protective equipment. Workers are at risk of HIV and HBV infection to the extent that they are directly exposed to blood and body fluids. Even in groups that presumably have a high potential for exposure to HIV-contaminated fluids and tissues, transmission is recognized as occuring only between sexual partners or as a consequence of mucous membrane or parenteral (including open wound) exposure to blood or other body fluids. In one investigation, of "needle stick" injuries, one health-care worker contracted HBV and in another instance, a health-care worker contracted cryptococcus. Both HBV and HIV appear to be incapable of penetrating intact skin, but infection may result from infectious fluids coming into contact with mucous membranes or open wounds on the skin.

A common medical practice by nurses and other hospital personnel charged with the responsibility of administering drugs by injection or withdrawing blood for lab work is to either dispose of a used needle by depositing it in a conventional "needle bucket", or "sharp bucket", or slipping the syringe and needle combination into a coat pocket for later disposal. These "sharp buckets" are normally located in each patient's room or on a cart which the nurse pushes from room to room. The bucket is later incinerated to destroy the contained needles. Another technique for disposing of used needles is the use of needle snips for clipping the needles from syringes after use and locating them in a container for later disposal and incineration. In view of the HIV and HBV contamination problem, nurses and hospital administrators, as well as doctors, laboratory technicians and others using syringes and needles, are extremely concerned about safety and liability. The nurses prefer not to use a cart for transporting a "sharp bucket" into the various rooms where patients are located and locating such buckets in the rooms sometimes results in other articles being placed therein by people who are unaware of the proper function for the "sharp bucket". This mingling of contents from previous injections and other disposable matter such as contaminated tissues and the like, creates the potential for mishandling or for the formation and growth of bacteria in the container. Furthermore, "sharp buckets" are not spillproof and needles can protrude through openings in the bucket or may be spilled from the bucket should the bucket be accidentally dropped or overturned, thereby further endangering the handler or handlers and contaminating the environment.

Various types of containers for medical equipment, as well as disposal of syringes, are known in the art. U.S. Pat. No. 620,434, dated Feb. 28, 1899 to G. Ermold, details a "Case for Hyperdermic Syringes". The case includes a base portion with a hinged lid which is constructed such that it can be disassembled, cleaned antiseptically and reassembled for conveniently carrying in a pocket. U.S. Pat. No. 685,091, dated Oct. 22, 1901, to M. W. Becton, details a "Surgical Instrument Case" which is also characterized by a base portion shaped to receive a surgical instrument and a hinged lid for closing over the base portion and the surgical instrument. An "Expanded Plastic Container Having Rigid Internally Press-Fit Cover" is detailed in U.S. Pat. No. 3,491,914, dated Jan. 27, 1970, to P.B. Elzey. The device is characterized by a molded, expandable plastic container having a chamber provided therein and fitted with an opening at one face or side, the periphery at the opening being recessed to define a flange and a supporting ledge. A flat lid is adapted to be inserted inside the flange and in engagement with the ledge, the lid being of such shape and dimension and having sufficient rigidity, such that it may be inserted within the flange in a press-fit and securely retained in place. U.S. Pat. No. 4,524,868, dated June 25, 1985, details a "Carrying Case For Pre-drawn Syringe". The carrying case is constructed of a flexible, resilient material and includes a liner made of an elastic material such as a foamed polyester. The liner includes a cut-out portion adapted to cradle a pre-drawn capped syringe. The case is of a size and dimension only slightly larger than the syringe itself and is intended to be carried in the purse or the pocket of a diabetic for injection of insulin. A "Needle Container and Method for Preventing Accidental Contact With a Needle" is detailed in U.S. Pat. No. 4,664,259, dated May 12, 1987, to Robert Landis. The needle container assures sterility of the needle prior to use and prevents inadvertent access to the needle after use. It includes a needle housing hingedly attached to a base, such that the housing may be moved from a first position covering the sterile needle to a second position exposing the needle for use, and then to a third position covering the used needle. A hook-like protrusion projects from the inside wall of the housing and is biased in a non-engaging relationship against the needle prior to use of the needle. When the housing is moved from the second to the third housing position, the hook-like protrusion engages the needle to prevent movement of the housing and further use of the needle. U.S. Pat. No. 4,671,408, dated June 9, 1987, to Kenneth Raines, et al, details a "Tamper-Resistant Protective Capping Device for Filled Syringes". The device includes a one-piece, molded product having a base section provided with a female port, a sterility protector and two side portions, which at their extended ends are further provided with complimentary locking structure. Accordingly, when a filled syringe is inserted in the female port at the base section of the unit, the two side portions can be hingedly folded therearound and closed to form a tamper-evident container for maintaining a filled syringe in tamper-proof, but reopenable condition. French Pat. No. 1,408,369, to M. Speitel, details a "Hyperdermic Container" which includes a base portion provided with a pair of receiving brackets therein and a top portion hinged to the base portion for enclosing the syringe when it is placed in the base portion.

It is an object of this invention to provide a syringe disposal container which is simple in design and totally protective in operation to prevent accidental needle pricks from contaminated needles.

Another object of the invention is to provide a new and improved syringe disposal container which is characterized by separate top and bottom portions, each provided with extending panel tabs and cooperating tab seats for locking together and enclosing a used syringe and needle to prevent re-use of the syringe and/or accidental needle sticks.

Yet another object of the invention is to provide a syringe disposal container which is characterized by separate top and bottom portions or panels fitted with a depression, cavity or receptacle for receiving a syringe and further including cooperating, spaced interlocking means provided in the panels for securing and encapsulating a syringe and needle therein, to prevent accidental pricking or sticking of doctors, laboratory technicians, hospital personnel and others charged with responsibility of using and handling syringes.

Still another object of the invention is to provide a new and improved syringe disposal container which is constructed of an injection-moldable plastic material and is characterized by separate top and bottom portions or panels, each fitted with a seal and interlocking tabs and corresponding tab seats, as well as an interior cavity or receptacle for locking the top and bottom panels together, encapsulating a used syringe and preventing reuse of the syringe and accidental sticking of those who use and handle syringes.

SUMMARY OF THE INVENTION

These and other objects of the invention are provided in a new and improved syringe disposal container which is characterized by a shaped bottom panel provided with a syringe cradle for receiving a syringe and needle and further fitted with a seal and spaced, extending lock tabs on one side thereof and tab seats on the opposite side for receiving and engaging corresponding tab seats and lock tabs, respectively, provided in a companion top panel having a seal and a syringe receptacle therein, whereby the top panel and bottom panel are locked together to enclose, seal and securely encapsulate the syringe and needle in the syringe cradle and receptacle for incineration.

BRIEF DESCRIPTION OF THE DRAWING

The invention will be better understood by reference to the accompanying drawing, wherein:

FIG. 1 is a perspective view of a preferred embodiment of the syringe disposal container of this invention;

FIG. 2 is a sectional view taken along line 2-2 of the bottom panel of the syringe disposal container illustrated in FIG. 1;

FIG. 3 is a sectional view taken along line 3-3 of the bottom panel of the syringe disposal container illustrated in FIG. 1; and FIG. 4 is a sectional view of the top panel closed on the bottom panel in locking configuration.

DESCRIPTION OF THE PRIOR ART

Referring initially to FIGS. 1 and 2 of the drawing, in a preferred embodiment the syringe disposal container of this invention is generally illustrated by reference numeral 1. The syringe disposal container 1 includes a rectangular-shaped bottom panel 2, provided with a bottom panel tab base 3 having a flat tab surface 3a extending along one face thereof and fitted with bottom panel tabs 4 projecting upwardly from the tab surface 3a in spaced relationship. Each of the bottom panel tabs 4 are characterized by an upward-standing tab post 5, having a bevelled post retainer 6 shaped in the extending end thereof. A bottom panel tab side 7 defines the side of the bottom panel tab base 3 and a bottom panel seat base 16 is located opposite the bottom panel tab base 3 in the bottom panel 2. Multiple bottom panel tab seats 17 are shaped in the bottom panel seat base 16 and each of the bottom panel tab seats 17 include a tab seat cavity 18, fitted with an encroaching retainer shoulder 19, as illustrated in FIG. 2. A bottom panel seat side 20 defines the side of the bottom panel seat base 16, as further illustrated in FIG. 2. A bottom panel front end 8, having a flat front end top surface 8a, closes the front end of the bottom panel 2 and a bottom panel rear end 9, having a flat rear end top surface 9a, closes the rear end of the bottom panel 2. A bottom panel tab 4 is provided in upward-standing relationship in each of the front end top surface 8a and the rear end top surface 9a, along with a corresponding bottom panel tab seat 17. As illustrated in FIG. 1, the respective bottom panel tabs 4 and bottom panel tab seats 17 located in the front end top surface 8a and the rear end top surface 9a are disposed in offset relationship with respect to each other. A syringe cradle 11 is shaped in the center of the bottom panel 2 and is characterized by a cradle bottom 12, supported by upward-standing cradle walls 13, which extend into the bottom panel tab base 3 on one side and the bottom panel seat base 16 on the opposite side, as well as the bottom panel front end 8 and the bottom panel rear end 9, respectively.

In a most preferred embodiment of the invention the bottom panel 2 is injection-molded from a suitable plastic material, such that the syringe cradle 11 is shaped in one piece with the bottom panel tab base 3, bottom panel seat base 16, bottom panel front end 8 and the bottom panel rear end 9. Furthermore, the bottom panel tabs 4 are also preferably molded or formed integrally with the bottom panel tab base 3, bottom panel front end 8 and the bottom panel rear end 9, while the bottom panel tab seats 17 are integrally shaped in the bottom panel seat base 16, bottom panel front end 8 and the bottom panel rear end 9. A cradle enlargement 14 is provided in the syringe cradle 11 adjacent to the bottom panel front end 8 and is designed to receive the barrel flange 47 of the syringe barrel 44 component of the syringe 43, which is fitted with a plunger 45 and a needle 46, as illustrated in phantom in FIG. 1.

Referring now to FIGS. 1 and 4 of the drawing, a top panel 25 is characterized by a top panel tab base 26 extending along one side thereof, with multiple top panel tabs 27 projecting downwardly from a flat top panel tab base face (not illustrated), in spaced relationship. As in the case of the bottom panel tabs 4, illustrated in FIG. 1, the top panel tabs 27 are each characterized by a tab post 5, downwardly-extending from the top panel tab base face, and fitted with a post retainer 6 on the end thereof. A top panel tab wall 28 defines an outside surface of the top panel tab base 26. A top panel seat base 37 extends along the opposite side of the top panel 25 and is provided with spaced top panel tab seats 38 therein. A top panel seat wall 39 defines the outside surface of the top panel seat base 37 and a top panel front end 29, having a flat bottom surface or face (not illustrated), closes the front end of the top panel 25. Similarly, a top panel rear end 30, also having a flat bottom surface (not illustrated), closes the rear end of the top panel 25. Oppositely-disposed, offset sets of top panel tabs (not illustrated) and top panel tab seats (not illustrated) are also provided in the bottom surfaces of the top panel front end 29 and the top panel rear end 30 for engagement with the respective bottom panel tab seats 17 and the bottom panel tabs 4, respectively, located in the front end top surface 8a and rear end top surface 9a, of the bottom panel front end 8 and bottom panel rear end 9, respectively, as hereinafter further described. A syringe receptacle 32 is also molded or otherwise provided in the top panel 25 and includes a receptacle top 33, supported by spaced receptacle walls 34, which are joined at the extending edges to the top panel tab base 26 and the top panel seat base 37, respectively. A receptacle enlargement 35 is also provided in the receptacle walls 34 of the syringe receptacle 32, as illustrated in FIG. 1.

Referring now to FIGS. 2–4 of the drawing, in a most preferred embodiment of the invention the cradle walls 13 of the syringe cradle 11 in the bottom panel 2 are each spaced from the bottom panel tab base 3 and the bottom panel seat base 16 by a separate bottom panel cavity 21. Similarly, the top panel tab base 26 and the top panel seat base 37 of the top panel 25 are each spaced from the respective facing receptacle walls 34 of the syringe receptacle 32 by a separate top panel cavity 40. The mold or molds used in injection-molding the bottom panel 2 and top panel 25 preferably shapes the bottom panel cavities 21 and top panel cavities 40, in order to avoid wasting plastic stock. However, it will be appreciated by those skilled in the art that the bottom panel 2 and top panel 25 can be injection-molded or otherwise fabricated without the bottom panel cavities 21 and top panel cavities 40, as desired.

In yet another most preferred embodiment of the invention, a bottom panel seal 22 projects upwardly from the tab surface 3a of the bottom panel tab base 3 and the bottom panel seat base 16, as well as the front end top surface 8a and the rear end top surface 9a of the bottom panel front end 8 and bottom panel rear end 9, respectively, around the periphery of the syringe cradle 11, as further illustrated in FIG. 1. Similarly, a top panel seal 41, illustrated in FIG. 4, projects from the bottom surfaces of the top panel tab base 26 and the top panel seat base 37, respectively, as well as the bottom surfaces of the top panel front end 29 and the top panel rear end 30, around the periphery of the syringe receptacle 32, in order to match the bottom panel seal 22 when the top panel 25 is fitted on the bottom panel 2, as hereinafter further described.

In operation and referring again to the drawing, when it is desired to close a syringe 43, fitted with the needle 46, inside the syringe disposal container 1 for permanent disposal, the syringe 43 is initially inserted in the syringe cradle 11 with the barrel flange 47 located in the cradle enlargement 14. The needle 46 therefore protrudes into the opposite end of the syringe cradle 11 from the barrel flange 47. The top panel 25 is then superimposed on the bottom panel 2 as illustrated in FIG. 1 and is then manipulated downwardly, such that the bottom panel tabs 4 and the top panel tabs 27 each project into a corresponding tab seat cavity 18 in the respective top panel tab seats 38 and bottom panel tab seats 17, as illustrated in FIG. 4. As the bottom panel tabs 4 travel upwardly and the top panel tabs 27 travel downwardly into the corresponding and aligned tab seat cavities 18, the respective retainer shoulders 19, located in the tab seat cavities 18, engage the corresponding post retainers 6, located on each tab post 5 of the bottom panel tabs 4 and the top panel tabs 27, respectively, and lock the respective bottom panel tabs 4 and top panel tabs 27 in the respective tab seat cavities 18. Due to the interlocking relationship between the flat portions of the respective post retainers 6 and retainer shoulders 19, the top panel 25 cannot then be removed from the bottom panel 2. Furthermore, due to the resulting tight contact between the bottom panel seal 22 and the corresponding top panel seal 41, the syringe 43 is sealed and encapsulated inside the syringe disposal container 1. The syringe disposal container 1 can then be placed in the pocket by a doctor, nurse, lab technician or other user or handler and subsequently tossed into a wastebasket or otherwise collected for incineration without fear of injury, reuse or contamination. While the bottom panel tabs 4 and top panel tabs 27 are illustrated in perpendicular extension from the respective tab bases, they can be angled to register with correspondingly angled top panel tab seats 38 and bottom panel tab seats 17, as desired. Other alterations, such as ribs on the bottom panel tabs 4 and top panel tabs 27 and corresponding multiple retainers or shoulders in the top panel tab seats 38 and bottom panel tab seats 17 may also be incorporated, in non-exclusive particular.

In a most preferred embodiment of the invention and referring again to the drawing, the bottom panel 2 and the top panel 25 of the syringe disposal container 1 are both injection-molded in a single mold from a suitable plastic material such as polyethylene or polypropylene, in non-exclusive particular. This facility reduces production costs, since the bottom panel 2 and the top panel 25 are identical, and therefore interchangeable. Alternatively, the syringe disposal container 1 can be fabricated in one or more molds from other materials, including fiberglass and like materials, according to the knowledge of those skilled in the art, under circumstances where the panel tabs are located on one panel and the tab seats on another. Furthermore, it is understood that the panel tabs and the tab seats may alternate one after another around each panel and match to corresponding panel tab seats and panel tabs, respectively. Moreover, while the bottom panel seal 22 and the top panel seal 41 are illustrated as flat on the matching top faces thereof, it is understood that other seal configurations, such as tongue-and-groove and the like, can be implemented, as desired.

It will be appreciated by those skilled in the art that the syringe disposal container of this invention is characterized by convenience, safety and portability, in that it can be quickly and easily used to protect and seal a used needle-equipped syringe without fear of contamination or needle pricks and without the necessity of separating the needle from the syringe. Accordingly, the syringe disposal container operates to prevent accidental infection and contamination of nurses, doctors, laboratory technicians and other medical personnel who are charged with the responsibility of using and handling syringes and needles. The syringe disposal container is universally sized, shatter-proof, leak-resistant and disposable.

While the preferred embodiments of the invention have been described above, it will be recognized and understood that various modifications may be made therein and the appended claims are intended to cover all such modifications which may fall within the spirit and scope of the invention.

Having described my invention with the particularity set forth above, what is claimed is:

1. A syringe disposal container for enclosing a syringe, comprising a bottom member, at least one lockable and non-releasable bottom member tab means upward-standing from said bottom member and at least one bottom member tab seat means provided in said bottom member in spaced relationship with respect to said bottom member tab means; and a top member, at least one lockable and non-releasable top member tab means downwardly projecting from said top member and at least one top member tab seat means provided in said top member in spaced relationship with respect to said top member tab means, whereby said bottom member tab means registers in locking, non-releasable relationship with said top member tab seat means and said top member tab means registers in locking, non-releasable relationship with said bottom member tab seat means for encapsulating the syringe when said top member is closed on said bottom member.

2. The syringe disposal container of claim 1 further comprising bottom member seal means provided on said bottom member for sealing the interface between said bottom member and said top member.

3. The syringe disposal container of claim 1 further comprising top member seal means provided on said top member for sealing the interface between said bottom member and said top member.

4. The syringe disposal container of claim 1 further comprising:
   (a) bottom member seal means provided on said bottom member; and
   (b) top member seal means provided on said top member for engaging said bottom member seal means and sealing the interface between said bottom member and said top member.

5. The syringe disposal container of claim 4 further comprising a cradle provided in said bottom member and a receptacle provided in said top member and wherein said bottom member seal means borders said cradle and said top member seal means borders said receptacle.

6. The syringe disposal container of claim 5 wherein said cradle and said receptacle are substantially identical in depth and configuration.

7. The syringe disposal container of claim 6 further comprising a cradle enlargement provided in said cradle and a receptacle enlargement provided in said receptacle for receiving and seating the barrel flange of the syringe.

8. The syringe disposal container of claim 1 wherein said at least one bottom member tab means further comprises a plurality of bottom member tabs disposed along one face of said bottom member in spaced relationship and said at least one top member tab seat means further comprises a plurality of top member tab seats disposed along one face of said top member in spaced relationship and wherein said one face of said bottom member is positioned opposite said one face of said top member in facing relationship, for registration of said bottom member tabs and said top member tab seats, respectively.

9. The syringe disposal container of claim 8 further comprising bottom member seal means provided on said bottom member for sealing the interface between said bottom member and said top member.

10. The syringe disposal container of claim 8 further comprising top member seal means provided on said top member for sealing the interface between said bottom member and said top member.

11. The syringe disposal container of claim 8 further comprising:
   (a) bottom member seal means provided on said bottom member; and
   (b) top member seal means provided on said top member for engaging said bottom member seal means and sealing the interface between said bottom member and said top member.

12. The syringe disposal container of claim 11 further comprising a cradle provided in said bottom member and a receptacle provided in said top member, and wherein said bottom member seal means borders said cradle and said top member seal means borders said receptacle.

13. The syringe disposal container of claim 1 wherein said at least one top member tab means further comprises a plurality of top member tabs disposed along one face of said top member in spaced relationship and said at least one bottom member tab seat means further comprises a plurality of bottom member tab seats disposed along one face of said bottom member in spaced relationship and wherein said one face of said top member is positioned opposite said one face of said bottom member in facing relationship, for registration of said top member tabs and said bottom member tab seats, respectively.

14. The syringe disposal container of claim 13 further comprising bottom member seal means provided on said bottom member for sealing the interface between said bottom member and said top member.

15. The syringe disposal container of claim 13 further comprising top member seal means provided on said top member for sealing the interface between said bottom member and said top member.

16. The syringe disposal container of claim 13 further comprising:
    (a) bottom member seal means provided on said bottom member; and
    (b) top member seal means provided on said top member for engaging said bottom member seal means and sealing the interface between said bottom member and said top member.

17. The syringe disposal container of claim 16 further comprising a cradle provided in said bottom member and a receptacle provided in said top member, and wherein said bottom member seal means borders said cradle and said top seal means borders said receptacle.

18. The syringe disposal container of claim 17 wherein:
    (a) said at least one bottom member tab means further comprises a plurality of bottom member tabs disposed along one face of said bottom member and on each end of said bottom member in spaced relationship and said at least one top member tab seat means further comprises a plurality of top member tab seats disposed along one face of said top member and on each end of said top member in spaced relationship and wherein said one face and said each end of said bottom member are positioned opposite said one face and said each end of said top member in facing relationship for registration of said bottom member tabs and said top member tab seats, respectively; and
    (b) said at least one top member tab means further comprises a plurality of top member tabs disposed along one face of said top member and on each end of said top member in spaced relationship and said at least one bottom member tab seat means further comprises a plurality of bottom member tab seats disposed along one face of said bottom member and on each end of said bottom member in spaced relationship and wherein said one face and said each end of said top member are positioned opposite said one face and said each end of said bottom member in facing relationship for registration of said top member tabs and said bottom member tab seats, respectively.

19. The syringe disposal container of claim 18 further comprising:
    (a) bottom member seal means provided on said bottom member; and
    (b) top member seal means provided on said top member for engaging said bottom member seal means and sealing the interface between said bottom member and said top member.

20. The syringe disposal container of claim 19 further comprising a cradle provided in said bottom member and a receptacle provided in said top member for receiving the barrel flange of the syringe in said bottom member and said top member.

21. The syringe disposal container of claim 20 wherein said bottom member seal means borders said cradle and said top seal means borders said receptacle.

22. A syringe disposal container for enclosing a syringe, comprising a first closure member and at least one tab projecting from said first closure member and lockable and non-releasable retaining means provided on said tab; a second closure member and at least one tab seat provided in said second closure member and shoulder means provided in said tab seat; a first receptacle provided in said first closure member and a second receptacle provided in said second closure member in alignment with said first receptacle for receiving the syringe, whereby said tab registers with said tab seat and said retaining means engages said shoulder means in lockable and non-releasable relationship for encapsulating the syringe in said first receptacle and said second receptacle when said first closure member is closed on said second closure member.

23. The syringe disposal container of claim 22 further comprising seal means provided on at least one of said first member and said second member for sealing the interface between said first member and said second member.

24. The syringe disposal container of claim 22 wherein said at least one tab further comprises a plurality of first member tabs disposed along a face of said first member in spaced relationship and said at least one tab seat further comprises a plurality of second member tab seats disposed along a face of said second member in spaced relationship and wherein said face of said first member is positioned opposite said face of said second member in facing relationship, for registration of said first member tabs and said second member tab seats, respectively.

25. The syringe disposal container of claim 24 wherein said receptacle means further comprises a first receptacle provided in said first member and a second receptacle provided in said second member, said second receptacle substantially matching said first receptacle, for receiving the syringe.

26. The syringe disposal container of claim 25 further comprising seal means provided on at least one of said first member and said second member for sealing the interface between said first member and said second member.

27. The syringe disposal container of claim 26 wherein said seal means further comprises a first seal provided on said first member bordering said first receptacle and a second seal provided on said second member bordering said second receptacle.

28. A syringe disposal container comprising an elongated bottom closure member; a plurality of bottom member tabs, each terminated by a bottom barbed tip, said bottom member tabs disposed along a first face of said bottom member in spaced relationship; a plurality of bottom member tab seats, each provided with a bottom internal shoulder, said bottom member tab seats disposed along a second face of said bottom member in spaced relationship; an elongated top closure member; a plurality of top member tabs, each terminated by a top barbed tip, said top member tabs disposed along a first face of said top member in spaced relationship; a plurality of top member tab seats, each provided with a top internal shoulder, said top member tab seats disposed along a second face of said top member in spaced relationship; and an elongated bottom receptacle provided in said bottom member and an elongated top receptacle provided in said top member for receiving a syringe, whereby said first face and said second face of said top member are oriented opposite said second face and said first face of said bottom member, respectively, in facing relationship and said bottom member tabs register with said top member tab seats and said bottom barbed tip locks into said top internal shoulder and said top member tabs register with said bottom member tab seats and said top barbed tip locks onto said bottom internal shoulder, respectively, for encapsulating the syringe in lockable and non-releasable relationship in said top receptacle and said bottom receptacle when said first member is closed on said second member.

29. The syringe disposal container of claim 28 further comprising:
   (a) a bottom member seal means provided on said bottom member; and
   (b) top member seal means provided on said top member for engaging said bottom member seal means and sealing the interface between said bottom member and said top member.

\* \* \* \* \*